United States Patent [19]

Buchwald et al.

[11] Patent Number: 5,004,820

[45] Date of Patent: Apr. 2, 1991

[54] PREPARATION OF CHIRAL METALLOCENE DIHALIDES

[75] Inventors: Stephen L. Buchwald; Robert B. Grossman, both of Somerville, Mass.

[73] Assignee: Massachusetts Institute of Technology, Cambridge, Mass.

[21] Appl. No.: 390,062

[22] Filed: Aug. 7, 1989

[51] Int. Cl.$^5$ .................................................. C07F 00/00
[52] U.S. Cl. ....................................................... 556/53
[58] Field of Search ........................................... 556/53

[56] References Cited

U.S. PATENT DOCUMENTS

| | | | |
|---|---|---|---|
| 4,169,845 | 10/1979 | Jonas | 556/53 X |
| 4,310,648 | 1/1982 | Shipley et al. | 526/114 |
| 4,361,685 | 11/1982 | Shipley | 526/114 |
| 4,404,344 | 9/1983 | Sinn et al. | 526/160 |
| 4,522,982 | 6/1985 | Ewen | 525/240 |
| 4,530,914 | 7/1985 | Ewen et al. | 502/113 |
| 4,701,432 | 10/1987 | Welborn, Jr. | 502/113 |
| 4,752,597 | 6/1988 | Turner | 502/104 |
| 4,874,880 | 10/1989 | Niya et al. | 556/53 |
| 4,892,851 | 1/1990 | Ewen et al. | 556/53 X |
| 4,910,121 | 3/1990 | Riediker et al. | 556/53 X |

FOREIGN PATENT DOCUMENTS

| | | | |
|---|---|---|---|
| 0035242 | 9/1981 | European Pat. Off. | 556/53 |
| 0279153 | 8/1985 | European Pat. Off. | 556/53 |
| 0277003 | 8/1988 | European Pat. Off. | 556/53 |
| 0277004 | 8/1988 | European Pat. Off. | 556/53 |
| 0284707 | 10/1988 | European Pat. Off. | 556/53 |
| 0284708 | 10/1988 | European Pat. Off. | 556/53 |

OTHER PUBLICATIONS

Wild et al., *J. Organomet. Chem.* 232 (1982) 233–47, Synthesis and Molecular Structures of Chiral ansa-Titanocene Derivatives with Bridged Tetrahydroindenyl Ligands.

Schafer et al., *J. Organomet. Chem.* 328 (1987) 87–99, Diastereomeric Derivatisation and Enantiometer Separation of Ethylenebis (Tetrahydroindenyl)–Titanium and –Zirconium Dichlorides.

Ewen et al., *J. Am. Chem. Soc.* 109 (1987) 6544, Crystal Structures and Stereospecific Propylene Polymerizations with Chiral Hafnium Metallocene Catalysts.

Collins et al., *J. Organomet. Chem.* 342 (1988) 21, X–Ray Structures of Ethylenebis (Tetrahydroindenyl)–Titanium and –Zirconium Dichlorides: A Revision.

*Primary Examiner*—Paul F. Shaver
*Attorney, Agent, or Firm*—Thomas J. Engellenner

[57] ABSTRACT

A process for preparing chiral metallocene dihalides as catalytic agents in improved yields by deprotonation of 1,2-bis(2,3-disubstituted cyclopentadienyl)ethane followed by condensation with hafnium tetrachloride or zirconium tetrachloride.

3 Claims, No Drawings

PREPARATION OF CHIRAL METALLOCENE DIHALIDES

The Government has rights in this invention pursuant to grant Number GM34917-05 awarded by the National Institutes of Health.

BACKGROUND OF THE INVENTION

This invention relates to an improved process for preparing chiral metallocene dihalides.

Chiral metallocene dihalides and derivatives are widely used as catalytic components in cocatalyzed polymerization reactions. In particular, transition metal-containing metallocene compounds are useful in conjunction with alumoxane cocatalysts in the polymerization of ethylene and the copolymerization of ethylene with 1-olefins or diolefins. Such catalyst systems are also useful in the production of isotactic polypropylene and other poly olefins.

Chiral metallocene dihalides such as ethylenebis($\eta^5$-indenyl)hafnium dichloride and ethylenebis($\eta^5$-indenyl)zirconium dichloride have been prepared by methods disclosed in Ewen et al., *J. Am. Chem. Soc.* 109: 6544 (1987) and Collins et al., *J. Organomet. Chem.* 342: 21 (1988), respectively, e.g., the deprotonation of 1,2-bis(3-indenyl)ethane with two equivalents of n-butyllithium followed by condensation with hafnium tetrachloride or zirconium tetrachloride. Although these prior art processes operate successfully, the yields are not optimum.

The process of this invention results in higher yields than the prior processes.

SUMMARY OF THE INVENTION

Chiral metallocene dihalides are produced by a new route from 1,2-bis(2,3-disubstituted cyclopentadienyl)ethane by deprotonation with potassium hydride followed by condensation with a Group 4 metal halide.

This invention provides a process for preparing, in improved yields, a chiral metallocene dihalide represented by the formula:

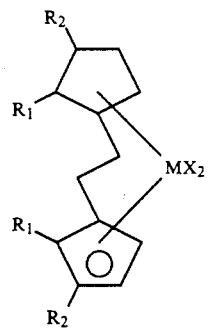

II wherein both $R_1$ and $R_2$, which can be the same or different, represent hydrocarbyl radicals such as alkyl, alkenyl, aryl, alkylaryl, or arylalkyl radicals having from 1 to 20 carbon atoms, and $R_2$ also represents hydrogen, or $R_1$ and $R_2$ are joined together with the two carbon atoms of the cyclopentadienyl ring form a $C_4$-$C_6$ ring; X is a halogen such as chlorine, bromine and iodine, and M represents zirconium or hafnium (except M is not zirconium when X is bromine).

Exemplary hydrocarbyl radicals are methyl, ethyl, propyl, butyl, amy 1, isoamyl, hexyl, isobutyl, octyl, nonyl, decyl, cetyl, 2-ethylhexyl, phenyl, and the like. Exemplary alkylene radicals are methylene, ethylene, propylene, butadienylene and the like. Exemplary halogen atoms include chlorine, bromine, and iodine.

DETAILED DESCRIPTION

The process of this invention comprises deprotonating a compound of Formula I with two equivalents of potassium hydride followed by condensation with a Group 4 metal halide to yield a chiral metallocene dihalide as illustrated in the following reaction scheme:

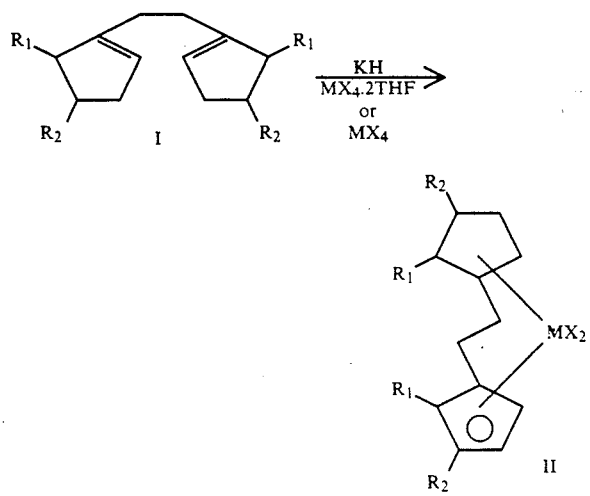

Wherein $R_1$, $R_2$, and M are as defined above.

Potassium hydride is suspended in an organic solvent such as tetrahydrofuran. Compound I is dissolved in an equivalent amount of organic solvent such as tetrahydrofuran and added to the potassium hydride suspension with evolution of hydrogen. $MX_4$ or its bis(tetrahydrofuran) adduct is also dissolved in an organic solvent such as tetrahydrofuran. Both solutions are added to a common organic solvent such as tetrahydrofuran, resulting in the formation of Compound II.

When Compound II is an ethylenebis-($\eta^5$-indenyl)-metal dihalide compound, it can be converted to an octahydro species, particularly useful for the production of isotactic polypropylene, by suspending Compound II in a hydrogenator in the presence of a platinum dioxide catalyst and an organic solvent such as methylene chloride. The hydrogenator is pressurized to about 1,000 psi hydrogen and left to stir for about eight hours. The resulting solution is diluted with a sufficient amount of methylene chloride and filtered. The filtrate is evaporated, leaving behind a solid material.

The following non-limiting examples further illustrate the invention:

EXAMPLE 1

Ethylenebis($\eta^5$-indenyl)zirconium dichloride 688 mg (17.2 mmol) potassium hydride was suspended in 20 ml of tetrahydrofuran. 2.01 g (7.78 mmol) 1,2-bis(3-indenyl)ethane was dissolved in 20 ml tetrahydrofuran and was added by cannula to the potassium hydride, resulting in an orange solution and white suspension changing to a green solution with large amounts of evolved hydrogen. 2.94 g (7.74 mmol) zirconium tetrachloride bis(tetrahydrofuran) adduct was dissolved in 45 ml tetrahydrofuran resulting in a colorless solution. The two solutions were added slowly and simultaneously to 50 ml tetrahydrofuran. The addition of the two solutions was completed after about an hour and a half. Anhydrous hydrogen chloride was bubbled through the solution, and then the solution was evaporated. The reaction mixture was then washed copiously with ether, followed by 5 ml of 4M hydrochloric acid chloride, 5 ml water, 5 ml ethanol, 5 ml ethanol, 5 ml ether, and 5 ml ether to give a yellow-orange powder. The resultant amount of product ethylenebis($\eta^5$-indenyl)zirconium dichloride was 2.464 g (5.89 mmol), 76% yield.

EXAMPLE 2

Ethylenebis($\eta^5$-tetrahydroindenyl)-hafnium dichloride 2.00 g (7.74 mmol) 1,2-bis(3-indenyl)ethane in 25 ml tetrahydrofuran was added to 688 mg (17.2 mmol) potassium hydride in 25 ml tetrahydrofuran. Also, 2.48 g (7.74 mmol) hafnium tetrachloride was dissolved in 100 ml tetrahydrofuran. An additional 50 ml of tetrahydrofuran was added to the 1,2-bis(3-indenyl)ethane and potassium hydride solution. The two solutions were added drop-wise to 100 ml of tetrahydrofuran at room temperature. The addition was complete after 1.5 hours. Gaseous hydrogen chloride was bubbled through the yellow solution. The solution was stripped down to give a brown-yellow oil. The oil was taken up in ether and filtered to give a yellow-white powder of ethylenebis($\eta^5$-indenyl)hafnium dichloride confirmed by NMR. The yellow-white powder was washed with two portions of 5 ml water, 2 portions of 5 ml ethanol, 5 and 10 ml portions of ether and then was dried with suction to give 1.501 g (3.02 mmol), 39% yield of ethylenebis($\eta^5$-indenyl)hafnium dichloride.

5.643 g (11.3 mmol) ethylenebis($\eta^5$-indenyl)-hafnium dichloride and 100 mg platinum dioxide were suspended in 70 ml methylene chloride and placed under 1500 psi hydrogen in a hydrogenator bomb. The reaction was run overnight, the pressure was released, and the solution was diluted with 300 ml methylene chloride and filtered through Celite. This solution was evaporated. Crystals were washed with ether to remove the silt and red color, resulting in 4.497 g (8.89 mmol), 78% yield of ethylenebis($\eta^5$-tetrahydroindenyl)hafnium dichloride, confirmed by NMR.

COMPARATIVE EXAMPLE

Ethylenebis($\eta^5$-indenyl)zirconium dichloride 5.00 g (19.3 mmol) 1,2-bis(3-indenyl)ethane dissolved in 125 ml tetrahydrofuran and 25.4 ml (38.6 mmol) of n-butyllithium were added together at −78° C. The solution was warmed to room temperature and was added drop-wise simultaneously with 4.56 g (19.4 mmol) zirconium tetrachloride bis(tetrahydrofuran) adduct in 125 ml tetrahydrofuran to 100 ml tetrahydrofuran at room temperature. The addition was complete after about two hours. Gaseous hydrogen chloride was bubbled through the solution until a color change (dark red-brown to yellow) was complete. The solution was evaporated. 5.95 g of solid was collected on a filter flask after diluting the yellow oily solid with ether. This material was washed with 10 ml of 4M hydrochloric acid, 10 ml water, 10 ml ethanol, 10 ml ethanol, 10 ml ether, and 10 ml ether to give 1.908 g (4.5 mmol), 24% yield of ethylenebis($\eta^5$-indenyl) zirconium dichloride as a powdery yellow solid. The resultant compound was identified by NMR. The yield was significantly less than that for the same compound in Example 1 of the present invention reported above.

We claim:

1. A process for preparing a chiral metallocene dihalide compound comprising reacting a compound represented by the formula:

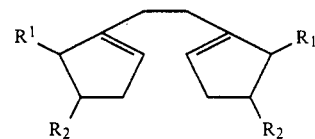

I wherein both $R_1$ and $R_2$, which can be the same or different, represent a hydrocarbyl radical such as alkyl, alkenyl, aryl, alkylaryl, or arylalkyl radicals having from 1 to 20 carbon atoms, and $R_2$ also represents hydrogen, or $R_1$ and $R_2$ are joined together with the two carbon atoms of the cyclopentadienyl ring form a $C_4$–$C_6$ ring; with potassium hydride followed by condensation with $MX_4$ or its bis(tetrahydrofuran) adduct, wherein X is a halogen selected from the group consisting of chlorine, bromine and iodine, and M represents zirconium or hafnium, except M is not zirconium when X is bromine, and recovering the resulting product.

2. The process of claim 1, wherein the reactants are 1,2-bis(3-indenyl)ethane, potassium hydride and hafnium tetrachloride or its bis(tetrahydrofuran) adduct.

3. The process of claim 1 wherein the reactants are 1,2-bis(3-indenyl)ethane, potassium hydride and zirconium tetrachloride or its bis(tetrahydrofuran) adduct.

* * * * *